Dec. 9, 1969 D. H. MOREY Plant Pat. 2,946
ROSE PLANT
Filed Oct. 26, 1967
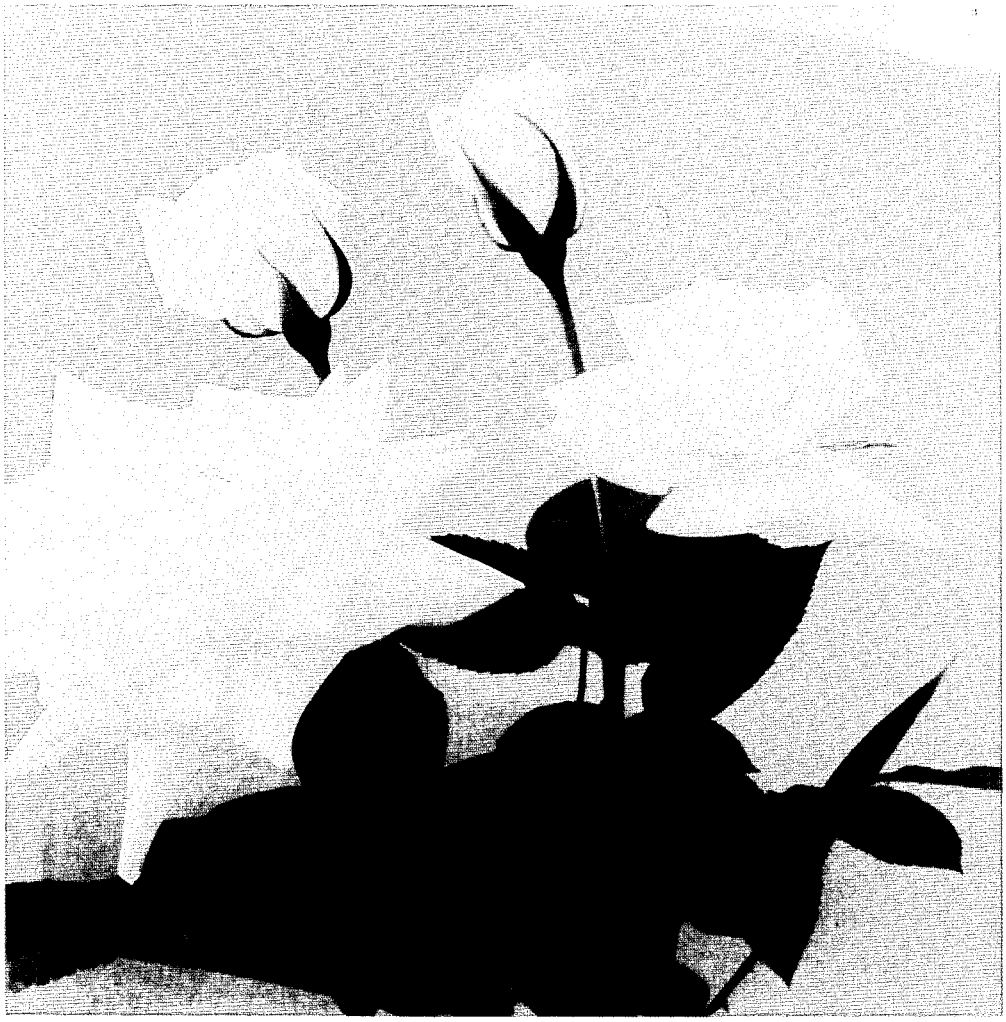

United States Patent Office

Plant Pat. 2,946
Patented Dec. 9, 1969

2,946
ROSE PLANT

Dennison H. Morey, 2750 Fulton Road,
Santa Rosa, Calif. 95404

Filed Oct. 26, 1967, Ser. No. 678,464
Int. Cl. A01h 5/02
U.S. Cl. Plt.—24 1 Claim The invention relates to a new and distinct variety of rose plant of the floribunda class originated by me in 1957 as a consequence of a breeding program begun in 1951. The parentage of my new rose plant is as follows: (Lydia × Golden Scepter) × Isobel Harkness.

The object of the cross was to produce a yellow rose of exceptional color intensity and color durability, profusely blooming on a dense compact plant with highly disease resistant dark lustrous foliage. These objectives were achieved along with other desirable improvements, as evidenced by the following unique combination of characteristics which are outstanding in the new variety and which distinguish it from its parents as well as from all other varieties of which I am aware. My new variety is primarily characterized by: vigorous bushy habit of growth; abundant disease resistant foliage, superior bud form and fidelity, and durability of flower color.

Asexual reproduction of my new variety by budding through a series of annual propagations at Livermore, Calif. shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of field and container growth budded plants under greenhouse and field conditions at Livermore, Ontario and Santa Rosa, Calif.

Vigorous, sturdy, upright bush to 20–30″ Moderate to heavy branching. Abundant foliage, odd pinnate and of smooth, leathery, glossy texture. Leaves are 3½–4¾″ long by 2–3″ wide. 3–5 leaflets, approximately 50% of each. Leaflets generally ovate with pointed tip and serrated margins. Spinach Green (HCC 0960/1) on upper side; Sage Green (HCC 000861/1) on underside. Petioles are ⅞–1⅜″ armed with from none to three small thorns. The ribs and veins are conspicuous. Rachis is 1–2½″ long armed with numerous thorns and prickles on under side and few thorns and prickles on the upper side. Rachis is pinkish green in color. Plant has approximately 6–15 thorns and prickles per 3″ of stem. Thorns are 3/16–½″ tall, 1/16–3/16″ wide and 3/16–⅓″ long with the point sticking straight out to curving down ⅔ of the height. The young thorns are Garnet Brown (HCC 00918); when mature, Straw to Tan.

Medium size bud 1¼–1½″ long by ⅝–⅞″ in diameter, opening slowly. Bud is long and pointed becoming urceolate. Chrome Yellow (HCC 605) streaked with Scheeles Green (HCC860/2) with tip of guard petal Brick Red (HCC 016/1) when sepals first divide. Same as above when sepals begin to unfurl. Sepals tend to hood over bud somewhat, moderately appendaged; very slightly branched, 1–2 very small branches per sepal. Minute prickles on margin of sepals. Spinach Green (HCC 0960/3) inside, Lettuce Green (HCC 861) outside. Calyx is funnel form to cup shaped of medium size, 7/16″ wide, 5/16″ long. Outside smooth, inside hairy.

Blooming habit recurrent spring through fall. Blooms borne 2–3 on strong canes. Medium sized flowers 3½–4⅜″ in diameter, 2–2½″ deep; high centered when bloom first opens, flattens somewhat as bloom matures. Petals imbricated, 27–32, soft to almost leathery, satiny in appearance, obovate. Outside petal is Barium Yellow (HCC 503/2) with the base Mimosa Yellow (HCC 602); inside petal is the same. Reverse side Mimosa Yellow (HCC 602/2). Petals are 1⅝–2⅛″ long, 1⅜—1 3/16″ wide. Slight fading after full bloom. Petaloids (staminodia) 2–4, 1⅛–1¼″ long by 3/16–¼″ wide; color like petals, but no streaking. Peduncle is sturdy, upright; has prickles, 2⅜–3 5/16″ long; Fern Green (HCC 0862/1). Bloom stays on plant 7–10 days finishes cleanly. Resistant to hot and cold weather. Moderate to strong tea rose fragrance. Stamens, anthers, about 86 in number, ½″ long, whorled arrangement. Filaments 7/16″ long, yellow in color. Pistils about 60 in number, about 5/16″ long. Stigmas orangish-pink to yellow in color. Orange pollen. Ovaries of ordinary character. Fruit is round, ⅝″ in diameter, yellow, sometimes russetted, sepals persist. Plant is immune to mildew and very resistant to other foliage problems such as rust and blackspot.

Having thus disclosed my invention, I claim:

1. A new and distinct variety of rose plant of the floribunda class substantially as herein shown and described primarily characterized by: vigorous bushy habit of growth; abundant disease resistant foliage, superior bud form and fidelity, and durability of flower color.

No references cited.

ROBERT E. BAGWILL, Primary Examiner.